United States Patent
Hsu

(10) Patent No.: US 7,438,925 B2
(45) Date of Patent: *Oct. 21, 2008

(54) DRUG ELUTING COATINGS FOR MEDICAL IMPLANTS

(75) Inventor: Li-Chien Hsu, Mission Viejo, CA (US)

(73) Assignee: Biovention Holdings Ltd., Hung Hom, Kowloon (HK)

( * ) Notice: Subject to any disclaimer, the term of this patent is extended or adjusted under 35 U.S.C. 154(b) by 224 days.

This patent is subject to a terminal disclaimer.

(21) Appl. No.: 10/423,718

(22) Filed: Apr. 26, 2003

(65) Prior Publication Data

US 2004/0037886 A1    Feb. 26, 2004

Related U.S. Application Data

(60) Provisional application No. 60/405,933, filed on Aug. 26, 2002.

(51) Int. Cl.
- A61F 13/00 (2006.01)
- A61F 2/00 (2006.01)
- A61K 9/00 (2006.01)

(52) U.S. Cl. .................. 424/422; 424/400; 424/423

(58) Field of Classification Search .................. 424/422, 424/400, 423
See application file for complete search history.

(56) References Cited

U.S. PATENT DOCUMENTS

| | | | |
|---|---|---|---|
| 3,663,288 A | 5/1972 | Miller | |
| 4,613,665 A | 9/1986 | Larm | |
| 4,634,762 A * | 1/1987 | Feijen et al. | 530/350 |
| 4,676,975 A | 6/1987 | McGary et al. | |
| 4,871,357 A * | 10/1989 | Hsu et al. | 604/266 |
| 5,047,020 A | 9/1991 | Hsu | |
| 5,061,738 A | 10/1991 | Solomon et al. | |
| 5,102,401 A * | 4/1992 | Lambert et al. | 604/264 |
| 5,112,457 A | 5/1992 | Marchant | |
| 5,288,711 A | 2/1994 | Mitchell et al. | |
| 5,356,433 A | 10/1994 | Rowland et al. | |
| 5,447,724 A | 9/1995 | Helmus et al. | |
| 5,455,040 A | 10/1995 | Marchant | |
| 5,464,650 A | 11/1995 | Berg et al. | |
| 5,496,832 A | 3/1996 | Armstrong | |
| 5,525,348 A * | 6/1996 | Whitbourne et al. | 424/423 |
| 5,609,629 A | 3/1997 | Fearnot et al. | |
| 5,665,728 A | 9/1997 | Morris et al. | |
| 5,716,981 A * | 2/1998 | Hunter et al. | 514/449 |
| 5,824,049 A | 10/1998 | Ragheb et al. | |
| 5,837,313 A | 11/1998 | Ding | |
| 5,919,762 A * | 7/1999 | Schweden et al. | 514/12 |
| 5,980,972 A | 11/1999 | Ding | |
| 6,120,536 A * | 9/2000 | Ding et al. | 623/1.43 |
| 6,179,817 B1 | 1/2001 | Zhong | |
| 6,231,600 B1 * | 5/2001 | Zhong | 623/1.42 |
| 6,251,136 B1 | 6/2001 | Guruwaiya et al. | |
| 6,258,121 B1 | 7/2001 | Yang et al. | |
| 6,273,913 B1 | 8/2001 | Wright et al. | |
| 6,299,604 B1 | 10/2001 | Ragheb et al. | |
| 6,306,166 B1 | 10/2001 | Barry et al. | |
| 6,309,660 B1 | 10/2001 | Hsu et al. | |
| 6,316,018 B1 | 11/2001 | Ding et al. | |
| 6,335,029 B1 | 1/2002 | Kamath et al. | |
| 6,344,035 B1 | 2/2002 | Chudzik et al. | |
| 6,749,626 B1 * | 6/2004 | Bhat et al. | 623/1.1 |
| 2001/0007083 A1 * | 7/2001 | Roorda | 623/1.15 |
| 2002/0133183 A1 * | 9/2002 | Lentz et al. | 606/155 |

FOREIGN PATENT DOCUMENTS

| | | |
|---|---|---|
| WO | WO9836784 | 8/1998 |
| WO | WO02062335 | 8/2002 |

OTHER PUBLICATIONS

Mehran R et al. Circulation 1990;100:1872-1878.
Schwartz RS. J Invas cardiol 1996;8:386-387.
Rogers C et al. Circulation 1993;88:1215-1221.
Serruys PW et al. N Eng J Med 1991;324:13-17.
Schatz RA et al. Circulation 1991;83:148-161.
Lablanche JM et al. Eur Heart J 1996;17:1373-1380.
Goods CM et al. Circulation 1996;93:1803-1808.
Mak KH et al. J Am Coll Cardiol 1996;27:494-503.
Hermanson GT et al. Immobilized Affinity Ligand Techniques. 1992;195-202. Academic Press.
Jozefonvicz et al.; Blood-Contacting Polymers; Polymeric Biomaterials; 1994; pp. 349-371; Marcel Dekker, Inc.; New York, New York.
Hsu; Biocompatibility in Cardiopulmonary Bypass; Journal of Cardiothoracic and Vascular Anesthesis; May 1997; pp. 376-382; vol. 11, No. 3.
van der Giessen et al.; Marked Inflammatory Sequelae to Implantation of Biodegradable and Nonbiodegradable Polymers in Porcine Coronary Arteries; Circulation; Oct. 1, 1996; pp. 1690-1697; vol. 94, No. 7.

* cited by examiner

Primary Examiner—Humera N Sheikh
(74) Attorney, Agent, or Firm—Steptoe & Johnson LLP

(57) ABSTRACT

Drug eluting coating compositions are composed of at least one therapeutic agent dispersed in modified, biologically active binders. The therapeutic agents included in the coating composition are paclitaxel, sirolimus, tacrolimus, everolimus, actinomycin-D, dexamethasone, mycophenolic acid, cyclosporins, estradiol, and derivatives and analogs thereof. These therapeutic agents are applied to the surface of the medical device by a modified, biologically active binders. By using these biologically active binders, the therapeutic agents can be applied to at least one surface of a medical implant without using inert polymer carriers.

12 Claims, No Drawings

DRUG ELUTING COATINGS FOR MEDICAL IMPLANTS

CROSS REFERENCE TO RELATED APPLICATIONS

This application claims the benefit of U.S. Provisional Application No. 60/405,933, filed Aug. 26, 2002, and whose entire contents are hereby incorporated by reference.

BACKGROUND

The implantation or insertion of a medical device into a patient's body can cause the body to exhibit adverse physiological reactions. The reactions may range from infections to the formation of emboli or clots in blood vessels. One particularly adverse physiological reaction is the result of epithelial damage to the cardiovasculature. That is, the vasculature can be damaged during procedures such as percutaneous transluminal coronary angioplasty (PCTA). As a result of damage to the epithelium of the vasculature, a cascade of physiological events may result in the re-narrowing (restenosis) of the vessel. While not completely understood, restenosis may be the result of smooth muscle cell proliferation in the intimal layers of the vessel.

Restenosis of an artherosclerotic coronary artery after PTCA occurs in 10-50% of patients undergoing this procedure and subsequently requires either further angioplasty or coronary artery bypass graft. In order to maintain the patency of the vessel, intravascular stents have been developed as a mechanical means of preventing the collapse or abrupt closure of the dilated segment of the artery.

Compared to PTCA, coronary stenting has a reduced restenosis rate. The angiographic restenosis rate for coronary stenting is about 10 to 20% in short lesions and large vessels. In-stent restenosis, however, occurs in over 30% to 60% of patients with diabetes, diffuse lesions, or lesions that occur in small vessels or are located at a bifurcation (Mehran R, et al. Circulation 1999; 100:1872-8). It is known that stenting prevents restenosis by eliminating negative remodeling and elastic recoil. However, stents fail to prevent neointimal proliferative response due to vessel injury. Studies have shown that stent-induced neointimal formation is more extensive and protracted than that provoked by PTCA (Schwartz R S. J Invas Cardiol 1996; 8:386-7; Rogers C, et al. Circulation 1993; 88:1215-21). In particular, intimal hyperplasia is the major component of late lumen loss after stent implantation.

Despite a high rate of procedural success with stent implantation, an unacceptably high (approximately 25%) rate of stent thrombosis is also experienced (Serruys P W et al. N Engl J Med 1991; 324: 13-7; Schatz RA et al. Circulation 1991; 83:148-61). With the use of aggressive and precise anti-platelet and anti-coagulation therapy along with the implementation of high pressure balloon expansion, recent studies have shown thrombosis rates of less than 2% when stents are implanted electively and thrombosis rates of less than 5% in the treatment of abrupt closure (Lablanche J M, et al. Eur Heart J 1996; 17:1373-80; Goods C M, et al. Circulation 1996; 93:1803-8). Although thrombosis rates are lower as compared to the results from the early studies, stent thrombosis is a disastrous complication that carries a high risk of ischemic sequelae. For example, data from several trials show rates of myocardial infarction and death of 61% and 12%, respectively (Mak KH et al. J Am Coll Cardiol 1996; 2 7:494-503). Additionally, systemic anti-platelet and anti-coagulation therapy increases the incidence of bleeding complications. Accordingly, there still remains a need for solution to stent thrombosis.

One approach to improve the biocompatibility of stents is to incorporate bioactive or pharmacological agents onto the stents. Various techniques have been utilized to immobilize bioactive agents onto relatively inert surfaces of stents. One such technique involves coupling bioactive agents onto stent surfaces via covalent bonding. For example, U.S. Pat. No. 4,613,665 issued to Larm describes the coupling of heparin with reactive aldehyde groups to an aminated surface. Also, U.S. Pat. Nos. 5,112,457 and 5,455,040 issued to Marchant disclose the use of a similar approach to end-bind heparin on modified substrates. The substrate modification consists of depositing a film of plasma polymerized N-vinyl-2-pyrrolidone and attaching a spacer (such as PEG) on the film. The end group of the spacer is a primary amine, which can be bonded to aldehyde-ended heparin through reductive amination.

While useful, the covalent bonding approach has various shortcomings. For instance, this approach generally involves a series of chemical reactions performed directly on the surfaces of the device which only allows a single layer of bioactive agents to be attached to the surfaces. As a result, limited amounts of bioactive agents may be applied to the surface of the stent. Moreover, if excessive reagents or reactants are used in the covalent bonding process, stent functionality can be compromised by minimizing the stent's ability to be fully expanded. Also, release of such active agents from the stent surface may not be possible or very limited because the active agents are chemically bonded to the stent surface.

An alternative method to covalent bonding approach involves physically blending or dispersing bioactive agent(s) with inert polymers. These "inert" polymers do not possess any known pharmacological activity and only serve as a carrier or binder for the bioactive agent(s). For instance, bioactive compounds such as heparin have been applied to stent surfaces utilizing inert polymers such as thermoplastic polyurethane, silicone, polycaprolactone, polylactic acid, polyethylene-vinyl acetate and cellulose-based polymers.

The use of inert polymers in drug coatings permits larger doses of drugs to be applied to the medical device surface and concomitantly larger amounts of the drugs may be released. However, there remains the difficulty of combining multiple drugs having different physical properties. For example, a hydrophobic drug and a hydrophilic drug could not be concomitantly applied because they are not miscible. In order to incorporate such a drug combination, multiple chemical reaction steps, or multiple physical deposition steps including micronizing the drug for dispersion are necessary. These multiple reaction/deposition steps generally are cumbersome and costly. Furthermore, the uniformity of the drug coating and drug release rates are often difficult to control. Thus, there still remains a need for uniform drug coatings that are capable of controllably delivering multiple drugs to a site of injury.

BRIEF SUMMARY

Embodiments of the drug releasing coatings described herein are uniform drug coatings capable of being applied to at least one surface of a medical device without the use of inert polymers. For example, exemplary embodiments of the drug releasing coatings do not require that the application of an inert polymer layer the surface of the medical device to bind a therapeutic agent to the medical device surface. Rather, the drug releasing coatings described herein utilized biologically active binders to apply one or more therapeutic agents to at least one surface of a medical device.

According to one exemplary embodiment, the drug releasing coating is composed of at least one therapeutic agent dispersed in modified, biologically active binders. For instance, the modified, biologically active binder may be a heparin complex such as, but not limited to, tertiary or quaternary ammonium complexes of heparin. These heparin complexes are generally hydrophobic thereby allowing the modified heparin to be a pharmacologically active carrier for hydrophobic therapeutic agents such as, but not limited to, anti-inflammatory, anti-proliferative, anti-migratiory, anti-neoplastic, anti-restenotic, immunosuppressive agents, or agents that promote healing and re-endothelialization. More specifically, the therapeutic agents may include, but are not limited to, paclitaxel, sirolimus, everolimus, tacrolimus, actinomycin-D, dexamethasone, mycophenolic acid, cyclosporins, estradiol, and their derivatives and analogs.

In another exemplary embodiment, the drug releasing coating includes a cap coating. The cap coating is applied over the drug releasing coating, and the cap coating acts as a barrier to allow for the controllable release of the therapeutic agent (and the bioactive binders) from the surface of the medical implant. According to one exemplary embodiment, the cap coating may be composed of ethylene vinyl acetate copolymers. In another exemplary embodiment, the cap coating may be composed of copolymers of ethylene and alkyl acrylate or polyalkylmethacrylate, wherein the alkyl group may be one to eight carbon atoms. In yet another exemplary embodiments, the cap coating may be composed of polyurethanes, copolymers of ethylene and propylene, styrene butadiene rubber, or silicone based polymers. As those skilled in the art will appreciate, the cap coating has elastomeric properties that allow the cap coating to be applied to expandable or flexible medical devices. Accordingly, the elastic properties of the cap coating permits the coating to be expanded and flexed without comprising the integrity of the cap coating thereby allowing for the controlled the release of the therapeutic agents (and biologically active binders) from the surface of the medical device. For non-flexible and non-expandable medical devices, non-elastomeric materials such as polycaprolactones can be used as a cap coating.

In another aspect, additional embodiments are directed to medical devices having a drug releasing coating capable of releasing at least one therapeutic agent while imparting anti-thrombotic properties to the surface of the medical devices. The coated medical devices include expandable prostheses such as, but not limited to, balloon expandable stents and self-expanding stents, stent grafts, vascular grafts, heart valves, heart valve sewing rings, annuloplasty rings, venous valves, sutures, sutureless coronary anastomosis devices connectors, implantable catheters and shunts, and other access devices. Alternatively, the compositions disclosed herein can also be incorporated into the bulk materials from which the prostheses are constructed.

In yet another aspect of the present invention, these medical implants can be delivered to a desired site within a patient's body. Once implanted, the therapeutic agents (and biologically active binders) that have been applied to the surface of the medical implant may elute from the surface of the implant. Accordingly, the controllable release of these components at the site of implantation may minimize any pathologies associated with the implantation of the device. Additionally, the therapeutic agents (and biologically active binders) may be controllably released from the surface of the medical implant by providing a cap coating on the medical implant.

DETAILED DESCRIPTION

Embodiments of the drug releasing coatings described herein and associated methods for their preparation can be used to deliver multiple drugs to a site of injury. Broadly, the coating compositions are composed of a modified, biologically active binders and at least one therapeutic agent dispersed in a substantially uniform manner within the binders. More specifically, the drug releasing coatings may be capable of delivering anti-restenotic agents to a localized site within a patient's body while providing anti-thrombotic properties to the medical device surface. Accordingly, thrombosis and restenosis that may be associated with medical device implantation (such as stent implantation) can be minimized by devices incorporating the drug releasing coating described herein.

According to one exemplary embodiment, the modified biologically active binder may be a modified heparin complex. That is, the heparin is modified to alter the hydrophilicity of the heparin. As those skilled in the art will appreciate, heparin is normally hydrophilic and is typically complexed with such counter ions as, sodium, lithium, zinc, or calcium. These heparin complexes may be modified into hydrophobic complexes by substituting the sodium or calcium with hydrophobic cations. For instance, according to one exemplary embodiment, the hydrophobic cations may be tertiary ammonium complexes. In another exemplary embodiment, the hydrophobic cations may be quaternary ammonium salts, such as, but not limited to, benzalkonium chloride, tridodecylmethyl ammonium chloride, stearylkonium chloride, cetylkonium chloride, and combinations thereof.

In yet another exemplary embodiment, the biologically active binder may be hydrophobically modified hirudin. Hirudin may be hydrophobically modified by reacting the amino acids on hirudin with hydrophobic compound(s). The side chains of amino acids 27 to 37 are particularly suitable for such modification as the modifications at these locations are less likely to affect the biological activity of hirudin. Coupling agents with spacer arms may also be used to react with the free N-terminal amino group, amino groups of the lysine side chains, amino groups of the histidines, amidine groups of the arginines. Hydrophobic groups can also be chemically linked to the hydroxyl groups of hirudin, such as tyrosine, serine or threonine side chains. It is preferred that the linkage of hydrophobic groups to hirudin leads to little or no loss of anti-thrombin activity. Examples of hydrophobic compounds are long chain substituted and/or unsubstituted fatty acids, fatty alcohols, or fatty amines. Various coupling agents, such as carbodiimides, tosyl chloride, and others can be used in peptide and protein immobilizations (Ref: Immobilized Affinity Ligand Techniques, Hermanson G T, et al, Academic Press Inc, 1992). Other peptide based anti-thrombotic or anti-platelet agents can be similarly modified to act as hydrophobic and pharmacologically active binder these hydrophobic complexes may be directly applied to the surfaces of a medical device.

Because the modified heparin complexes and the modified hirudin molecules are hydrophobic, these substances are soluble in organic solvents such as, but not limited to, halogenated hydrocarbons, aromatic and aliphatic hydrocarbons, alcohols, cyclic ethers, ketones, such as methylene chloride, ethanol, tetrahydrofuran and 1,1,2 trichloroethane. When the hydrophobicity of the modified binders "matches" that of therapeutic agent(s) to be incorporated, the compatibility of the "binder" and the therapeutic agent is greatly enhanced. The enhanced compatibility leads to the formation of a homogenous mixture, which results in a uniform coating.

Furthermore, the closely matched hydrophobicity between the active binder and therapeutic agent also provides a similar and predictable release rate upon exposure of the coating to physiological environment.

Consequently, any hydrophobic therapeutic agents may also be dissolved in common organic solvents with these modified heparin and/or hirudin complexes. These therapeutic agents include, but are not limited to, paclitaxel, rapamycin (sirolimus), everolimus, tacrolimus, actinomycin-D, dexamethasone, mycophenolic acid, cyclosporins, estradiol, or combinations thereof. Accordingly, both the biologically active binders and the therapeutic agents can be concomitantly applied to the surface of a medical device. Furthermore, the relative ratio of the binders (modified heparin) to the therapeutic agent can be easily varied depending on the type of medical devices and anticipated pathophysiological problems associated with the implant devices.

The ability to eliminate inert polymer carrier enhances the bioactivity of the coating composition and minimizes potential adverse physiological reactions to the inert polymer carrier. The composition also minimizes the thickness of coating thereby limiting the impact of coating on profile of the coated devices. The composition also allows for the incorporation of two distinctly different pharmacological agents (e.g., an anti-thrombotic agent and an anti-angiogenic agent) onto/into the prostheses in one step. Thus, the various embodiments of drug coatings avoid the necessity of multiple chemical reaction steps or multiple physical deposition steps that are generally required to incorporate the two types of pharmacological agents. Embodiments disclosed herein further provide compositions and methods that avoid the need of micronizing heparin, a hydrophilic drug and only soluble in water, in order to be incorporated into a hydrophobic drug (anti-angiogenic agent, such as paclitaxel and sirolimus), which are in general only soluble in organic solvents.

Appropriate amounts of therapeutic agent and biologically active binders are dissolved in a common organic solvent. A composite drug coating solution is obtained after all drugs are dissolved. The coating solution can be applied on a device, such as stent, by spray coating. After the solvent in the coating solution is evaporated, a thin layer of coating remains on the surface of the device. The process can be repeated as many times as desired. A waiting period may or may not be required, depending on the volatility of the solvent system used. Alternatively, the coating can also be applied to the medical device by dip-coating. Dip-coating is especially useful for devices that are not conducive to being spray-coated such as, but not limited to, vascular grafts and stent grafts. Brush-coating can be used. A swab saturated with coating solution can be applied to the devices. The coating may also be applied by using a combination of spraying, dipping, and brushing.

Depending on the desired release rate of drugs, after the composite drug coating is deposited onto the device, an additional polymer coating layer may be applied to the drug composite to further regulate the release of the drug composite. Such polymer coating may be either a biostable or a biodegradable polymer. Biostable polymers generally considered to be biocompatible such as, but not limited to, polyurethanes, silicones, ethylene-vinyl acetate copolymer, polyethers such as homopolymers or copolymers of alkylene oxide, homo- or copolymers of acrylic, polyamides, polyolefins, polyesters, polydienes, cellulose and related polymers. Bioabsorbable polymers that could be used include poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-cotrimethylene carbonate), polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid. These and other polymer systems can be used if they can be dissolved or dispersed in a solvent system that can be applied to the drug composite without causing adverse effect on the composite. Generally, conventional coating techniques, such as spray-coating, dip-coating, or brush-coating can be employed to apply the polymer coating.

In another aspect of the present invention, methods of minimizing restenosis and thrombosis are disclosed herein. Generally, when the coating compositions are applied to at least one surface of the implantable devices, the coatings can simultaneously prevent thrombosis and restenosis without using "inert" polymer carriers, which are generally required for drug eluting coatings. More specifically, according to one exemplary method, the medical implant is provided with at least one uniform coating that is composed of modified heparin complex and at least one therapeutic agent such as paclitaxel, rapamycin (sirolimus), tacrolimus, everolimus, actinomycin-D, dexamethasone, mycophenolic acid, cyclosporins, estradiol, or combinations thereof. The medical implant having the drug releasing coating may be delivered and implanted at a desired site within the patient's body by any method known or developed in the art. Once implanted, the therapeutic agents and/or the modified heparin complexes may be controllably released from the surface of the medical implant to minimize restenosis and thrombosis.

While several embodiments have been described, those skilled in the art will appreciate that various substitutions, omissions, modifications and changes which may be made without departing from the scope or spirit thereof. Accordingly, it is intended that the foregoing description be considered merely exemplary and not a limitation thereof. A further understanding of the drug releasing coatings and associated methods will be afforded to those skilled in the art from the following non-limiting examples:

EXAMPLE 1

Paclitaxel and Stearylkonium Heparin

Paclitaxel (Sigma Aldrich, St. Louis, Mo.) and stearylkonium heparin (as prepared according to U.S. Pat. No. 5,047,020, whose entire contents are incorporated by reference) at a weight ratio of 50/50 were dissolved in methylene chloride. The coating solution was then sprayed onto the surface of a 9 mm long balloon expandable stainless steel coronary stent. The spraying was conducted in such a way that substantial all exposed surfaces of the stent were covered with the solution and that a desired amount of drug loading on the stent was achieved. The coated stent was then dried in an oven at about 50° C. for 2 hours or until all solvent is evaporated. The coverage of coating on the surfaces of the stent was examined by using heparin or a cation sensitive dye.

EXAMPLE 2

Paclitaxel and Benzalkonium Heparin

Paclitaxel (Sigma Aldrich, St. Louis, Mo.) and benzalkonium heparin at a weight ratio of 75/25 were dissolved in ethanol. A 9 mm long balloon expandable stainless steel coronary stent mount on a mandrel was then dip-coated in the solution. The coated stent was then rotated on the mandrel at a low rpm until all solvent was evaporated. Slow rotation while drying ensures an even distribution of the drug components. The dip-coating steps can be repeated until a desirable drug loading is accomplished.

EXAMPLE 3

Dexamethasone and Tridodecylmethyl Ammonium Heparin

Dexamethasone and tridodecylmethyl ammonium heparin (TDMAC heparin) at a weight ratio of 25/75 were dissolved in tetrahydrofuran. The coating solution was then sprayed onto the surface of a balloon expandable stainless steel coronary stent. The spraying was conducted in such a way that substantial all exposed surfaces of the stent were covered with the solution and that a desired amount of drug loading on the stent was achieved. The coated stent was then dried in an oven at about 50° C. for 2 hours or until all solvent is evaporated. The coverage of coating on the surfaces of the stent was examined by using heparin or cation sensitive dye.

EXAMPLE 4

Rapamycin and Benzalkonium Heparin

Rapamycin and benzalkonium heparin at a weight ratio of 50/50 were dissolved in 1,1,2 trichloroethane. The coating solution was then sprayed onto the surface of a balloon expandable stainless steel coronary stent. The spraying was conducted in such a way that substantial all exposed surfaces of the stent were covered with the solution and that a desired amount of drug loading on the stent was achieved. The coated stent was then dried in an oven at about 50° C. for 2 hours or until all solvent is evaporated. The coverage of coating on the surfaces of the stent was examined by using heparin or cation sensitive dye.

EXAMPLE 5

Top Coat (Ethylene Vinyl Acetate Copolymer)

An appropriate amount of ethylene vinyl acetate copolymer was dissolved in methylene chloride to yield a 2.5% (wt/vol) polymer solution. The solution was sprayed to the stent prepared according to that described in example 4 until a thin layer of top coat is uniformly deposited on the drug-coated stent. The coated stent was then dried until all solvent is evaporated. This top coating further regulates the drug release rate.

EXAMPLE 6

Top Coat (Polycaprolactone)

An appropriate amount of polycaprolactone was dissolved in methylene chloride to yield a 5% (wt/vol) polymer solution. The solution was sprayed to the stent prepared according to that described in Example 1 until a thin layer of cap coat is uniformly deposited on the drug-coated stent. The coated stent was then dried until all solvent is evaporated. This top coating further regulates the drug release rate.

EXAMPLE 7

Paclitaxel (Sigma Aldrich, St. Louis, Mo.) and stearylkonium heparin at a weight ratio of 50/50 were dissolved in methylene chloride. An expanded ePTFE stent graft is immersed in the solution briefly and dried subsequently to evaporate off the solvent. The coated stent graft is then briefly dipped in a polymer solution containing ethylene vinyl acetate copolymer and subsequently dried.

EXAMPLE 8

Rapamycin and benzalkonium heparin at a weight ratio of 25/75 were dissolved in 1,1,2 trichloroethane. A polyester knit suture ring for heart valve is dip-coated in the solution and dried. The coated suture ring is then dip-coated in biodegradable elastomeric copolymer of caprolactone and glycolide in acetone (5%, wt/vol) and subsequently dried.

What is claimed is:

1. A coating composition, consisting essentially of:
   a dispersion of hydrophobically-modified heparin and at least one hydrophobic therapeutic agent, wherein the hydrophobically-modified heparin is a complex of heparin and tertiary or guaternary ammonium salts, wherein the hydrophobic therapeutic agent reduces restenosis, wherein the hydrophobically-modified heparin is a carrier for the therapeutic agent, and wherein the at least one therapeutic agent is elutable from the dispersion.

2. The coating composition of claim 1, wherein the modified heparin is selected from the group consisting of stearylkonium heparin, benzalkonium heparin, cetylkonium heparin, and tridodecylmethyl ammonium heparin.

3. The coating composition of claim 1, wherein the therapeutic agent is selected from the group consisting of paclitaxel, sirolimus, tacrolimus, everolimus, dexamethasone, mycophenolic acid, cyclosporins, and estradiol.

4. A medical device comprising:
   a body having at least one surface; and
   a coating layer directly applied to the least one surface, wherein the coating layer consists essentially of a dispersion including hydrophobically-modified heparin and at least one hydrophobic therapeutic agent dispersed therein, wherein the hydrophobically-modified heparin is a complex of heparin and tertiary or guaternary ammonium salts, wherein the hydrophobic therapeutic agent reduces restenosis, wherein the hydrophobically-modified heparin is a carrier for the therapeutic agent, and wherein the at least one therapeutic agent is elutable from the coating layer.

5. The medical device of claim 4, wherein the modified heparin is selected from the group consisting of stearylkonium heparin, benzalkonium heparin, cetylkonium heparin and tridodecylmethyl ammonium heparin.

6. The medical device of claim 4, wherein the hydrophobic therapeutic agent is selected from the group consisting of paclitaxel, sirolimus, tacrolimus, everolimus, dexamethasone, mycophenolic acid, cyclosporins, and estradiol.

7. A coating composition, consisting essentially of:
   hydrophobically-modified, biologically active binders comprising hydrophobic cations coupled to heparin, the hydrophobic cations being tertiary ammonium complexes or guaternary ammonium complexes; and
   one or more hydrophobic therapeutic agents, wherein the hydrophobic therapeutic agents are elutable from hydrophobically-modified, biologically active binders, wherein the hydrophobic therapeutic agent reduces restenosis, and wherein the hydrophobically-modified heparin is a carrier for the therapeutic agent.

8. The coating composition of claim 7. wherein the quaternary ammonium salts are benzalkonium chloride, tridodecylmethyl ammonium chloride, stearylkonium chloride, cetylkonium chloride, or combinations thereof.

9. The coating composition of claim 7. wherein the hydrophobic therapeutic agent is selected from the group consisting of paclitaxel, sirolimus, tacrolimus, everolimus, dexamethasone, mycophenolic acid, cyclosporins, and estradiol.

10. The coating composition of claim 1, wherein the hydrophobically- modified heparin is also elutable from the coating composition.

11. The coating composition of claim 4, wherein the hydrophobically-modified heparin is also elutable from the coating layer.

12. A medical device, comprising:
a body having one or more surfaces; and
a coating composition associated with the one or more surfaces of the body, wherein the coating composition consisting essentially of a dispersion of hydrophobically-modified heparin and at least one hydrophobic therapeutic agent, wherein the hydrophobically-modified heparin is a complex of heparin and tertiary or guaternary ammonium salts, wherein the hydrophobic therapeutic agent reduces restenosis, wherein the hydrophobically-modified heparin is a carrier for the therapeutic agent, and wherein the hydrophobically-modified heparin and the at least one hydrophobic therapeutic agent is also elutable from the coating composition.

* * * * *

UNITED STATES PATENT AND TRADEMARK OFFICE
CERTIFICATE OF CORRECTION

PATENT NO. : 7,438,925 B2  
APPLICATION NO. : 10/423718  
DATED : October 21, 2008  
INVENTOR(S) : Li-Chien Hsu It is certified that error appears in the above-identified patent and that said Letters Patent is hereby corrected as shown below:

Column 8  
In line 24, replace "guaternary" with --quaternary--  
In line 45, replace "guaternary" with --quaternary--  
In line 63, replace "guaternary" with --quaternary--

Column 10  
In line 9, replace "guaternary" with --quaternary--

Signed and Sealed this

Sixteenth Day of December, 2008

JON W. DUDAS  
*Director of the United States Patent and Trademark Office*